United States Patent [19]

Yamasaki et al.

[11] Patent Number: 5,480,891
[45] Date of Patent: Jan. 2, 1996

[54] METHOD FOR TREATING DIABETES MELLITUS

[75] Inventors: Katsuya Yamasaki; Kazushi Sakurai; Kazue Akiyama, all of Tokushima, Japan

[73] Assignee: Otsuka Pharmaceutical Co., Ltd., Japan

[21] Appl. No.: 159,703

[22] Filed: Dec. 1, 1993

Related U.S. Application Data

[63] Continuation of Ser. No. 978,696, filed as PCT/JP92/00689, May 28, 1992, abandoned.

[30] Foreign Application Priority Data

Jun. 7, 1991 [JP] Japan ..................... 3-136465

[51] Int. Cl.⁶ .................................... A61K 31/47
[52] U.S. Cl. .............................. 514/312; 514/313
[58] Field of Search ................. 514/235.2, 253, 514/312, 313

[56] References Cited

U.S. PATENT DOCUMENTS 4,578,381  3/1986  Uchida et al. ............... 514/235.2

FOREIGN PATENT DOCUMENTS

| | | |
|---|---|---|
| 53-012872 | of 1978 | Japan . |
| 53-009777 | 1/1978 | Japan . |
| 54-098779 | 8/1979 | Japan . |
| 63-35623B2 | 7/1988 | Japan . |
| 3-74329 | 3/1991 | Japan . |
| 3-74329A | 3/1991 | Japan . |
| 3-145468A | 6/1991 | Japan . |

OTHER PUBLICATIONS

Effect of OPC–12759, a Novel Antiulcer Agent, On Chronci And Acute Experimental Gastric Ulcer, And Gastric Secretion In Rats, Yamasaki et al., Japan J. Pharmacol., 49:441–448 (1989).

Chemical Abstracts, vol. 75, No. 5, Aug. 2, 1971, Abstract No. 35805s.

European Journal of Pharmacology, vol. 53, No. 4, 1979, pp. 351–358.

*Primary Examiner*—Marianne M. Cintins
*Assistant Examiner*—K. Weddington
*Attorney, Agent, or Firm*—Finnegan, Henderson, Farabow, Garrett & Dunner

[57] ABSTRACT

A method for treating diabetes mellitus comprising administering to a patient in need thereof a pharmaceutically acceptable inert carrier in combination with an effective amount for treating diabetes mellitus of a carbostyril compound or a pharmaceutically acceptable salt thereof of the formula:

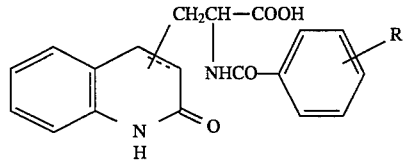

wherein R is a halogen atom, the position of substitution of the side chain in the carbostyril skeleton being at the 3- or 4-position and the bond between the 3-position and the 4-positions in the carbostyril skeleton being a single bond or a double bond.

4 Claims, No Drawings

METHOD FOR TREATING DIABETES MELLITUS

This application is a continuation of application Ser. No. 07/978,696, filed as PCT/JP92/00689, May 28, 1992, now abandoned.

TECHNICAL FIELD

The present invention relates to an anti-diabetes mellitus and more particularly it relates to an anti-diabetes mellitus comprising as active ingredient a carbostyril derivative represented by the general formula (1), or a salt thereof:

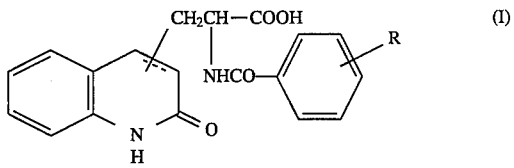

(wherein R is a halogen atom, the position of substitution by the side chain on the carbostyril skeleton is the 3-position or the 4-position, and the carbon atom bond between the 3-position and the 4-position of the carbostyril skeleton is a single bond or a double bond), preferably 2-(4-chlorobenzoylamino)-3-(2-quinolon-4-yl)propionic acid or a salt thereof.

BACKGROUND ART

Carbostyril derivatives represented by the above general formula (1) and a production process thereof are described in Japanese Patent Kokoku (Post-Exam. Publn.) No. 63-35623 (U.S. Pat. No. 4,578,381), and they are known to be useful as anti-ulcerative agents.

In addition, Japanese Patent Kokai (Laid-Open) No. 3-74329 discloses an invention relating to a different use (an agent for treating gastritis) of the same compound as used in the present invention, Japanese Patent Kokai (Laid-Open) No. 3-145468 discloses an invention of a process for producing an optically active substance of the compound used in the present invention, and Japan. J. Pharmacol. Vol. 49, pp. 441–448 (1989) discloses that the compound used in the present invention has activity for inhibiting active oxygen.

According to the classification of diseases of WHO (United Nations-World Health Organization), diabetes mellitus is classified into insulin dependent diabetes mellitus (IDDM) in which acute or sub-acute symptoms are shown owing to the insufficiency of the absolute quantity of insulin and treatment by administration of insulin is necessary; non-insulin dependent diabetes mellitus (NIDDM) in which the progress of diabetes mellitus is slow and treatment by administration of insulin is not always necessary; malnutrition-related diabetes mellitus (MRDM); and chronic hyperglycemia accompanying other maladies and syndromes.

Of these, IDDM is considered to be attributable to the disruption of pancreatic β-cells by autoimmune mechanism. HLA (human leukocyte antigen), cytocaine, virus, etc. are regarded as causes of the disruption of pancreatic β-cells (Koji Nakanishi, Tetsuro Kobayashi and Mitsuru Hara "TONYOBYO GAKU (Diabetes mellitus), 1989" edited by Mikinori Kosaka and Yasuo Akanuma, published by "SHIN-DAN-TO-CHIRYO SHA", 1989, pp. 226–244).

On the other hand, as the cause of NIDDM, there are considered to exist, for example, insulin-effect disorders caused by various factors such as (1) congenital disorders in pancreas, i.e., disorders of adaptability to an increase of the demand for insulin, and (2) aging, obesity, stress, etc. (Hiroo Imura "TONYOBYO GAKU-NO-SIMPO" (Progress in Treatment of Diabetes Mellitus), 1989, edited by Japan Diabetes Society, published by "SHINDAN-TO-CHIRYO SHA", 1989, pp. 1–12).

However, the onset of diabetes mellitus including IDDM and NIDDM is due to the tangle of hereditary factors and environmental factors, and a considerable part of the onset remains unknown.

PROBLEMS TO BE SOLVED BY THE INVENTION AND MEANS FOR SOLVING THEM

In the course of various studies for developing an anti-diabetes mellitus, the present inventors found that a carbostyril derivative represented by the above general formula (1), in particular, 2-(4-chlorobenzoyl-amino)-3-(2-quinolon-4-yl)propionic acid or a salt thereof, is excellent in activity for lowering blood sugar and activity for protecting pancreas β-cells, has activity for lowering blood sugar and inhibitory effect for increasing insulin value in blood in a pharmacological test using NIDDM-rats OLETF (Otsuka Long Evans Tokushima Fatty) (Kawano, K.; Hirashima, T.; Mori, S.; Kurosumi, M.; Saitoh, Y.; RATS NEWS LETTER, No. 25, pp. 24–26, July, 1991.), and is useful as a preventive and curative drug against insulin dependent diabetes mellitus and non-insulin dependent diabetes mellitus, whereby the present invention has been accomplished.

The anti-diabetes mellitus of the present invention is obtained by formulating a carbostyril derivative of the above general formula (1) or a salt thereof into a conventional medicinal preparation form. Such a parathion is prepared using conventional diluents or excipients, such as fillers, bulking agents, binding agents, wetting agents, disintegrating agents, surface active agents, lubricating agents and the like. As the medicinal preparation, various forms can be chosen depending on therapeutical purposes, and typical examples of the preparation form are tablets, pills, powders, liquids, suspensions, emulsions, granules, capsules, suppositories, injections (solutions, suspensions, etc.), and the like.

In the case of shaping into the tablet form, as carriers, various carriers heretofore well known to the art can be used, and there can be exemplified excipients such as lactose, white sugar, sodium chloride, glucose, urea, starch, calcium carbonate, kaoline, crystalline cellulose, silicic acid and the like; binding agents such as water, ethanol, propanol, simple syrup, glucose solutions, starch solutions, gelatin solutions, carboxymethyl cellulose, shelac, methyl cellulose, potassium phosphate, polyvinyl pyrrolidone and the like; disintegrating agents such as dried starch, sodium alginate, agar-agar powder, laminaria powder, sodium bicarbonate, calcium carbonate, esters of polyoxyethylene sorbitan fatty acids, sodium laurylsulfate, stearic acid monoglyceride, starch, lactose and the like; disintegration inhibiting agents such as white sugar, stearin, coconut butter, hydrogenated vegetable oil and the like; absorption promotors such as quaternary ammonium basis, sodium laurylsulfate and the like; wetting agents such as glycerin, starch and the like; adsorbing agents such as starch, lactose, kaoline, bentonite, colloidal silicic acid and the like; lubricants such as purified talc, stearates, boric acid powder, polyethylene glycols and the like. In addition, if necessary, the tablets can be made into coated tablets having a usual coating, for example, tablets coated with sugar, tablets coated with gelatin film, tablets coated with enteric coating layer, tablets coated with films or double layer tablets as well as multiple layer tablets, and the like.

In the case of shaping into the pill form, as carriers, various carriers heretofore well known to the art can be used, and there can be exemplified excipients such as glucose, lactose, starch, coconut butter, hydrogenated vegetable oil, kaoline, talc and the like; binding agents such as gum arabic powder, tragacanth gum powder, gelatin, ethanoland the like; disintegrating agents such as laminalan, agar-agar and the like.

In the case of shaping into the suppository form, as carriers, various heretofore well-known carriers can be used, and there can be exemplified polyethylene glycols, coconut butter, higher alcohols, esters of higher alcohols, gelatin, and semi-synthesized glyceride.

In the case of formulation into the injection, the solution and the suspension are sterilized and are preferably isotonic to the blood. For shaping into any of the solution, emulsion and suspension forms, as a diluent, all of those usually used in the art can be used, and there can be exemplified water, ethyl alcohol, propyleneglycol, ethoxylated isostearyl alcohol, polyoxylated isostearyl alcohol, and polyoxyethylene sorbitan fatty acid esters. In this case, sodium chloride, glucose or glycerin may be incorporated into the curative drug in an amount sufficient to prepare an isotropic solution, and the curative drug may be incorporated with conventional dissolving auxiliaries, buffer solutions, analgesic agents, and optionally coloring materials, preservatives, perfumes, seasoning agents, sweetening agents and other medicines.

Although the amount of the carbostyril derivative (1) or salt thereof to be contained in the anti-diabetes mellitus of the present invention is not critical and is chosen in a wide range, it is usually 1 to 70% by weight, preferably 5 to 50% by weight based on the weight of the whole composition.

A method for administering the anti-diabetes mellitus of the present invention is not critical, and the anti-diabetes mellitus is administered by a method suitable for any of various pharmaceutical forms, the age, sex and other conditions of a patient, the degree of disease, etc. For example, when the anti-diabetes mellitus is any of tablets, pills, a solution, a suspension, an emulsion, granules and capsules, it is orally administered. When the anti-diabetes mellitus is an injection, it is administered intravenously singly or in admixture with usual injectable transfusions of glucose, amino acid, etc., and if necessary, it is administered alone intramuscularly, intracutaneously, subcutaneously or intraperitoneally. When the anti-diabetes mellitus is a suppository, it is administered into rectum.

Although the dose of the anti-diabetes mellitus of the present invention is properly chosen depending on administration route, the age, sex and other conditions of a patient, the degree of disease, etc., the amount of the carbostyril derivative (1) or salt thereof is usually preferably 0.6 to 50 mg per kg of body weight a day. It is preferable to incorporate 10 to 1,000 mg of the active ingredient into an administration unit form.

EXAMPLES

The anti-diabetes mellitus of the present invention is more concretely explained below with reference to formulation examples and pharmacological experiments.

Formulation Example 1

| | |
|---|---|
| 2-(4-Chlorobenzoylamino)-3-(2-quinolon-4-yl)propionic acid | 150 g |
| Avicel (a trademark for microcrystalline cellulose, manufactured by Asahi Chemical Industry Co., Ltd.) | 40 g |
| Corn starch | 30 g |
| Magnesium stearate | 2 g |
| Hydroxypropylmethyl cellulose | 10 g |
| Polyethylene glycol 6000 | 3 g |
| Castor oil | 40 g |

-continued

| | |
|---|---|
| Methanol | 40 g |

The compound according to the present invention, Avicel, corn starch and magnesium stearate are mixed and ground, then the mixture is tableted by using a pounder (R 10 mm) for sugar coating. The resulting tablets are coated with a film coating agent composed of hydroxypropylmethyl cellulose, polyethylene glycol 6000, castor oil and methanol to produce film-coated tablets.

Formulation Example 2

| | |
|---|---|
| 2-(4-Chlorobenzoylamino)-3-(2-quinolon-4-yl)propionic acid | 150 g |
| Citric acid | 1.0 g |
| Lactose | 33.5 g |
| Dicalcium phosphate | 70.0 g |
| Pluronic F-68 | 30.0 g |
| Sodium lauryl sulfate | 15.0 g |
| Polyvinylpyrrolidone | 15.0 g |
| Polyethylene glycol (Carbowax-1500) | 4.5 g |
| Polyethylene glycol (Carbowax-6000) | 45.0 g |
| Corn starch | 30.0 g |
| Dried sodium lauryl sulfate | 3.0 g |
| Dried magnesium stearate | 3.0 g |
| Ethanol | q.s. |

The compound according to the present invention, citric acid, lactose, dicalcium phosphate, Pluronic F-68 and sodium lauryl sulfate are admixed together.

The above mixture is sieved through No. 60 sieve, then the sieved mixture is wet granulated with an alcoholic solution containing polyvinylpyrrolidone, Carbowax-1500 and -6000. The granulated product is made into a paste-like lump by adding ethanol, if necessary. Corn starch is added thereto and mixing is continued until uniform granules are formed. The granules are passed through No. 1 sieve, and the granules sieved are placed in a tray and dried in an oven at 100° C. for 12 to 14 hours. The dried granules are sieved through No. 16 sieve, and dried sodium lauryl sulfate and dried magnesium stearate are added to and mixed with the thus sieved granules, after which the resulting mixture is compressed into a desired shape by using a tablet machine.

The core portions described above are treated with a varnish, and sprinkled with talc to prevent the absorption of moisture. The periphery of the core portions is coated with a primary coating layer. A sufficient number of varnish coating operations for oral administration are carried out. For obtaining completely spherical and smooth tablets, primary coating layers and smoothing coating are further given. Color-coating is conducted until a desired color is obtained. After drying, the coated tablets are given a uniform gloss.

Formulation Example 3

| | |
|---|---|
| 2-(4-Chlorobenzoylamino)-3-(2-quinolon-4-yl)propionic acid | 5 g |
| Polyethylene glycol (Molecular weight: 4,000) | 0.3 g |
| Sodium chloride | 0.9 g |
| Polyoxyethylene sorbitan monooleate | 0.4 g |
| Sodium metabisulfite | 0.1 g |

| | |
|---|---|
| Methyl para-hydroxybenzoate | 0.18 g |
| Propyl para-hydroxybenzoate | 0.02 g |
| Distilled water for injection | 10.0 ml |

The above-mentioned para-hydroxybenzoates, sodium metabisulfite and sodium chloride are dissolved in about one-half of the above amount of distilled water at 80° C. with stirring. The resulting solution is cooled to 40° C., after which the compound according to the present invention and then polyethylene glycol and polyoxyethylene sorbitan monooleate are dissolved in the solution. Subsequently, distilled water for injection is added to the resulting solution to prepare a final volume of a solution, and this solution is sterilized by means of sterilizing filtration using a suitable filter paper to prepare an injection preparation.

Pharmacological Experiment 1

Alloxan was intravenously administered to Wistar-strain male rats (body weight: about 240 g, Japan SLC) at a dose of 40 mg/kg to prepare alloxan-induced diabetes rats.

As a test compound, 2-(4-chlorobenzoylamino)-3-(2-quinolon-4-yl)propionic acid (hereinafter referred to as compound A) according to the present invention was intraperitoneally administered to said rats at a dose of 100 mg/kg twice, i.e., simultaneously with and 8 hours after the administration of alloxan, and the rats were fed under non-fast condition. After 24 hours, blood was sampled from artery, whereby blood plasma was obtained. The blood sugar (glucose) level in the blood plasma was measured by the glucose oxidase method, and the plasma insulin was also measured. The results are shown in Table 1. Results obtained when the test compound had not been administered are also shown therein as the results of a control test.

TABLE 1

| Test compound | Blood glucose level (mg/dl) | Blood plasma insulin (μ unit/ml) |
|---|---|---|
| Control | 491 ± 21 | 14 ± 1 |
| Compound A | 224 ± 18 | 22 ± 2 |

As indicated by the above experimental results, in a group to which the compound according to the present invention had been administered, the increase in the blood glucose level by the administration of alloxan was suppressed, and the decrease in insulin was also suppressed.

Pharmacological Experiment 2

1) Animal used:
OLETF rats (7 weeks old), 10 males.
2) Drug used:
Compound A was used at a dose of 30 mg/kg in the form of a suspension prepared by suspending compound A in a 0.5% carboxymethyl cellulose solution so that the suspension might be used in an amount of 2 ml/kg.
3) Experimental method:
The rats were divided into two groups of 5 rats each as follows.
(1) Compound A was intraperitoneally administered to the rats in a test group at a dose of 30 mg/kg time a day.
(2) Physiological saline was intraperitoneally administered to the rats in a control group once a day.

An oral glucose tolerance test (OGTT) was carried out 1 month, 2 months and 3 months after the administration of the drug. In the OGTT, glucose was orally administered by force to the rats which had been fasted for 16 hours, and blood was sampled from the tail vein before the loading and 30, 60, 90 and 120 minutes after the loading. The blood glucose level was measured by the GOD-POD (glucose oxidase-peroxidase) method by using Glucose B-test Kit Wako (manufactured by Wako Pure Chemical Industries, Ltd.). The insulin level in blood plasma was measured by an RIA method [an insulin-measuring kit manufactured by Baxter Co. (USA)] before the glucose loading and 60 and 120 minutes after the glucose loading.

As to a standard of judgement on diabetes mellitus, when in the OGTT, the highest value of the blood glucose level was 300 mg/dl or more and its value after 120 minutes was 200 mg/dl or more, the rats were judged to have diabetes mellitus. The intraperitoneal administration on the day of the OGTT was carried out after completion of all the blood-sampling operations. The results are shown in Table 2.

The sum of the glucose levels in blood plasma before the glucose loading and 30, 60, 90 and 120 minutes after the glucose loading was taken as the total amount of glucose in blood plasma. The results are shown in Table 3.

The sum of the insulin levels in blood plasma before the glucose loading and 60 and 120 minutes after the glucose loading was taken as the total amount of insulin in blood plasma. The results are shown in Table 4.

4) Experimental results

TABLE 2

| Period | Group | Number of laboratory animals | Incidence of diabetes mellitus (%) |
|---|---|---|---|
| 1 Month | Control | 5 | 0 |
| | Compound A | 5 | 0 |
| 2 Months | Control | 5 | 100 |
| | Compound A | 5 | 20 |
| 3 Months | Control | 5 | 40 |
| | Compound A | 5 | 0 |

TABLE 3

| Period | Group | Total amount of glucose in blood plasma (ml/dl × 5) |
|---|---|---|
| 1 Month | Control | 1,072 |
| | Compound A | 915 |
| 2 Months | Control | 1,404 |
| | Compound A | 1,070 |
| 3 Months | Control | 1,379 |
| | Compound A | 1,048 |

TABLE 4

| Period | Group | Total amount of insulin in blood plasma (pg/ml × 3) |
|---|---|---|
| 1 Month | Control | 6,423 |
| | Compound A | 7,079 |
| 2 Months | Control | 10,381 |
| | Compound A | 7,679 |
| 3 Months | Control | 14,250 |
| | Compound A | 8,044 |

We claim:
1. A method for treating non-insulin dependent diabetes mellitus comprising administering to a patient in need thereof a pharmaceutically acceptable inert carrier in com- bination with an effective amount for treating non-insulin dependent diabetes mellitus of a carbostyril compound or a pharmaceutically acceptable salt thereof, of the formula:

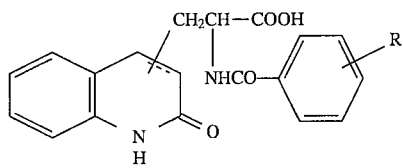

wherein R is a halogen atom, the position of substitution of the side chain in the carbostyril skeleton being at the 3- or 4-position and the carbon-carbon bond between the 3- and 4-positions in the carbostyril skeleton being a single or double bond.

2. The method for treating non-insulin dependent diabetes mellitus of claim 1, wherein the carbostyril compound is 2-(4-chlorobenzoylamino)-3-(2-quinolon-4-yl)propionic acid or pharmaceutically acceptable salt thereof.

3. A method for treating insulin dependent diabetes mellitus comprising administering to a patient in need thereof a pharmaceutically acceptable inert carrier in combination with an effective amount for treating insulin-dependent diabetes mellitus of a carbostyril compound or a pharmaceutically acceptable salt thereof, of the formula:

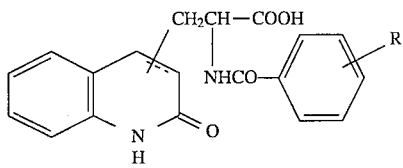

wherein R is a halogen atom, the position of substitution of the side chain in the carbostyril skeleton being at the 3- or 4-position and the carbon-carbon bond between the 3- and 4-positions in the carbostyril skeleton being a single or a double bond.

4. The method for treating insulin-dependent diabetes mellitus of claim 3, wherein the carbostyril compound is 2-(4-chlorobenzoylamino)-3-(2-quinolon-4-yl)-propionic acid or a pharmaceutically acceptable salt thereof.

* * * * *